US008527293B2

(12) United States Patent
Hammond et al.

(10) Patent No.: US 8,527,293 B2
(45) Date of Patent: Sep. 3, 2013

(54) METHOD AND SYSTEM FOR SUPPORTING CLINICAL DECISION-MAKING

(75) Inventors: Christopher Reynolds Hammond, Schenectady, NY (US); Brion Daryl Sarachan, Schenectady, NY (US); Matthew David Kelly, Oxford (GB); Rachel Susannah Midgley, Oxford (GB); John Michael Brady, Headington (GB); Mark Robert Austin, Middlesex (GB); David J. Kerr, Oxford (GB)

(73) Assignee: General Electric Company, Schenectady, NY (US)

( * ) Notice: Subject to any disclaimer, the term of this patent is extended or adjusted under 35 U.S.C. 154(b) by 1340 days.

(21) Appl. No.: 11/731,157

(22) Filed: Mar. 30, 2007

(65) Prior Publication Data

US 2008/0243542 A1  Oct. 2, 2008

(51) Int. Cl.
 *G06Q 10/00* (2012.01)
(52) U.S. Cl.
 USPC .................................... 705/2; 705/3
(58) Field of Classification Search
 USPC ........................................................ 705/2, 3
 See application file for complete search history.

(56) References Cited

U.S. PATENT DOCUMENTS

| 5,953,704 | A | * | 9/1999 | McIlroy et al. ................... 705/2 |
| 6,149,585 | A |   | 11/2000 | Gray |
| 6,820,067 | B1 |   | 11/2004 | Hammond |
| 7,577,573 | B2 | * | 8/2009 | Janas et al. ........................ 705/2 |
| 2002/0091687 | A1 |   | 7/2002 | Eglington |
| 2004/0039602 | A1 |   | 2/2004 | Greenberg |
| 2004/0260576 | A1 |   | 12/2004 | Wang |
| 2004/0260700 | A1 |   | 12/2004 | Wang |
| 2004/0261063 | A1 |   | 12/2004 | Wang |
| 2006/0100738 | A1 | * | 5/2006 | Alsafadi et al. ............... 700/214 |

FOREIGN PATENT DOCUMENTS

| WO | WO 2005/059803 | 6/2005 |
| WO | WO 2006/013515 | 2/2006 |
| WO | WO 2006/013516 | 2/2006 |
| WO | WO 2006/035383 | 4/2006 |

OTHER PUBLICATIONS

Pages retrieved from http://www.openclinical.org, last visited on Mar. 17, 2008.
Open Clinical: White Paper; http://www.openclinical.org/whitepaper.html, 2008.
Open Clinical: Methods and tools for representing computerized clinical guidelines; http://www.openclinical.org/gmmsummaries.html, 2008.
Open Clinical: Method and tools for the development of computer-interpretable guidelines; the Guideline Interchange Format (GLIF); http://www.openclinicai.org/gmm_glif.html, 2008.

(Continued)

*Primary Examiner* — Michael Fuelling
(74) *Attorney, Agent, or Firm* — Hanley, Flight and Zimmerman, LLC

(57) ABSTRACT

A method and system are provided for facilitating decision making, such as in a clinical setting. In accordance with this technique, a set of encoded guidelines are executed to identify information that may be used to generate patient management options. The information is acquired, if available. Based on the encoded guidelines and the acquired information, a set of patient management options are generated and provided to one or more reviewers for review and selection of a patient management option.

17 Claims, 7 Drawing Sheets

(56) References Cited

OTHER PUBLICATIONS

Open Clinical: Method and tools for the development of computer-interpretable guidelines (ASBRU); http://www.openclinical.org/gmm_asbru.html, 2008.

Open Clinical: Method and tools for the development of computer-interpretable guidelines; standards-based Share4able Active Guideline Environment (SAGE); http://www.openclinical.org/gmm_sage.html.

Open Clinical: Method and tools for the development of computer-interpretable guidelines; (GUIDE); http://www.openclinical.org/gmm_guide.html, 2008.

Open Clinical: Method and tools for the development of computer-interpretable guidelines; format knowledge representation method for the development and execution of clinical guidelines (PROforma); http://www.openclinical.org/gmm_proforma.html, 2008.

Machado, Lucila Ohno, et al.; The GuideLine Interchange Format: A Model for Representing Guidelines; pp. 1-34.

Peleg, Mor, PhD, et al.; Comparing Computer-interpretable Guideline Models: A Case-study approach; Journal of American Medical Informatics Association, vol. 10, No. 1, Jan./Feb. 2003, pp. 52-68.

Fox, John, et al.; a general technology for clinical decision support systems; Computer Methods and Programs in Biomedicine 54 (1997), pp. 59-67.

* cited by examiner

FIG. 2

| PATIENT MODE | JOHN DOE 49 MALE | T2↓N0 M0 | DOWNSTAGED |

SUMMARY | HISTORY | INVESTIGATIONS | DECISIONS

MR. DOE PRESENTED WITH RECTAL
BLEEDING AND WEIGHT LOSS AND WAS
FOUND TO HAVE A LOW RECTAL CANCER. HE
IS A FATHER OF TWO AND A SUCCESSFUL BUSINESSMAN.
HE HAS UNDERGONE RADIOCHEMOTHERAPY AND IS NOW
BEING CONSIDERED FOR SURGERY.

SURNAME: DOE
FORENAME: JOHN
AGE: 49
WHO PERFORMANCE STATUS: 0
SYMPTOMS: UNEXPLAINED WEIGHT LOSS
            RECTAL BLEEDING
FAMILY MEMBERS WITH CRC: NO
2 WEEK WAIT: YES

PRE OP
+PATIENT 1
+PATIENT 2

DOWNSTAGED
JOHN DOE
SUMMARY
HISTORY
INVESTIGATIONS
DECISION

PAST OP
+PATIENT 3
+PATIENT 4

PRELOAD
MEETING
ANALYSIS

METHOD AND SYSTEM FOR SUPPORTING CLINICAL DECISION-MAKING

BACKGROUND

The invention relates generally to the management of the treatment of diseases in a multidisciplinary framework.

As advances in medical knowledge and techniques are made, the amount of information available when treating a patient, as well as the number of patient management options available, have steadily increased. As a result, patient management for many diseases may benefit from review of an ever-increasing amount of patient data in order to identify the most appropriate patient management options. Furthermore, the amount of data available to be considered is growing not only in quantity, but also in diversity, as, for example, new imaging technologies and drugs are introduced. As a result, no single clinician can have mastered the diversity of information to be considered in treating certain diseases.

For example, for diseases such as cancer, patient management may involve a team of clinicians spanning a range of specialisations. Such a multidisciplinary team (MDT), in the exemplary context of cancer patient management, may include one or more surgeons, radiologists, oncologists, clinical pharmacologists, pathologists, and so forth. The MDT may meet (this may be a face-to-face meeting, a teleconference, or an electronic meeting (e.g. over the internet)) regularly to collectively review a patient's clinical data and select the optimal patient management option. In this manner, the MDT can pool their expertise to jointly determine the next step in patient management. For these meetings to be effective, the team of clinicians should be presented with all of the data (such as patient records, imaging studies, drug information, and so forth) relevant to the decisions to be made. Further, accurate records should be kept of decisions made and the identities of the clinicians present.

Currently, MDTs collect the data necessary to make decisions for groups of patients by manually assembling the information that they believe is relevant to the decision making process and presenting it to the group of clinicians making the decision. Relevant information may be overlooked or unavailable at the time of the meeting, which may result in a delay in the meeting while the necessary information (such as radiological scans) is accessed or a delay in patient care due to postponement of a patient management decision until the next meeting. Alternatively, if such overlooked or unavailable information is not properly taken into account in the decision making process, an inappropriate patient management decision may be made due to the failure to consider all relevant information, including information that is not known or available, that might change the patient management decision.

In current practice, such team-analysis and/or team-decision making may be relatively informal and/or unstructured, with different team members being present at successive meetings and/or with little or no record of individual preferences or exceptions to the team's majority or consensual decisions. For example, a given discipline (such as surgery or oncology) may be represented by different individuals at different meetings such that new participants have little, very limited or insufficient history with the patient, and no recollections of previous discussions about the patient. Further, individual comments endorsing or disagreeing with the team decision are not typically noted, so future team meetings do not have the benefit of such prior discussion. Instead, it is currently assumed all members of the team support the final decision, with no mechanism in place for recording potential disagreements between specialists. In addition, the information the MDT bases its decision on may be incomplete or poorly organized, making proper analysis of the information difficult and/or inefficient. Despite this, the MDT is expected to review all aspects of the data, assess its potential impact on present and future clinical decisions, and ensure that errors due to information on which the decision is known to be contingent not being taken into account are minimized.

Further, the team decision process is typically not completely based on the latest evidence related to the disease. Likewise, there is no assurance that the most recent guidelines are followed to ensure the same standard of care for all patients. Instead decisions are often based upon the participant's specific experiences and knowledge, without regard to how representative the clinician's experiences or knowledge may be or to the biases in decision making that may be introduced by such reliance on personal experience. Further, when the latest guidelines are followed, they are often not sufficiently prescriptive and are sometimes contradictory. As such, they have to by supplemented with clinician preference.

BRIEF DESCRIPTION

The present technique is generally directed to facilitating group review of a set of options, such as the review of patient management options by an MDT or other collaborative decision making group in a medical context. In accordance with one aspect of the present technique, a set of encoded guidelines are executed to identify information that may be used to generate patient management recommendations based upon a decision to be made. The identified information is gathered, if available. Based on the acquired information, and taking into account information that may have been unavailable but was identified as being of interest, the guidelines are executed to generate one or more patient management options and corresponding recommendations. The patient management options and recommendations are provided to the reviewers to select a patient management option. In certain embodiments, the reviewers are also provided with information such as the acquired information used to generate the patient management options and recommendations and/or an indication of information that may be of interest but is unavailable. The selected patient management decision is stored for future reference. In certain embodiments, other information may also be stored for future reference, such as what reviewers concurred or dissented from the decision and what comments or rationales were provided by the reviewers in support of or against the decision or in support of a non-selected patient management option. In some implementations, this representation of the decision history that can be displayed in a form to enable rapid and accurate recall of decisions at previous meetings, acting as a corporate or institutional memory. Likewise, this representation of the decision history may also be utilized for the automatic generation of reports and/or in the creation of an audit trail.

For example, in one embodiment, the present technique is directed to a method for generating patient management options. The method includes the act of identifying information to be obtained. The information is identified based at least on a set of encoded guidelines. The information that is available is electronically acquired. One or more patient management recommendations are generated by analyzing the acquired information based on the set of encoded guidelines. The one or more patient management recommendations are provided to one or more decision makers. A corresponding computer program and processor-based system are also provided.

In another exemplary embodiment, the present technique is directed to a method for reviewing a decision making process. The method includes the act of generating one or more patient management recommendations based on an analysis of available patient-specific information using encoded guidelines. A patient management option is selected after reviewing the one or more patient management recommendations. The act of selecting is performed by one or more reviewers. Commentary is provided related to the selection of the patient management option. At least the one or more patient management recommendations, the selected patient management option, and the commentary are electronically stored. The selection of the patient management option is audited based upon at least the stored patient management recommendations, the stored selected patient management option, and the stored commentary.

Likewise, a computer program is provided encoded on one or more computer readable media. The computer program includes a routine configured to generate one or more patient management recommendations using a set of encoded guidelines and available patient-specific information. Routines are also provided which are configured to provide at least the one or more patient management recommendations to one or more reviewers and to receive a selection of a patient management option from the one or more reviewers. The computer program also includes routines configured to receive commentary related to the selection from at least one of the reviewers and to store at least the one or more patient management recommendations, the selection, and the commentary. A routine configured to audit the selection of the patient management option based upon at least the stored patient management recommendations, the stored selection, and the stored commentary is also provided. A corresponding processor-based system is also provided.

DRAWINGS

These and other features, aspects, and advantages of the present invention will become better understood when the following detailed description is read with reference to the accompanying drawings in which like characters represent like parts throughout the drawings, wherein:

FIG. 2 is an exemplary screenshot of a patient summary for review in selecting a patient management option, in accordance with exemplary embodiments of the present technique;

DETAILED DESCRIPTION

In one embodiment, the present technique provides a platform for the automatic integration and presentation of the diverse kinds of information used in making clinical decisions or other decisions typically made in a multidisciplinary context. In addition, embodiments of the present technique maintain a detailed record of decisions and the decision-making process and provide decision support based on accepted guidelines, such as published clinical guidelines. To provide additional usefulness, systems implemented in accordance with the present technique may provide a rationale or explanation for recommendations and may be configured to display data influencing, positively or negatively, the decision being made. The decision, data, and justification for the decision, along with any dissenting comments may be stored for audit or for subsequent review, such as at the next decision-making meeting. While the present discussion generally describes implementations in the context of clinical multidisciplinary team decision making, such implementations are merely illustrative. Indeed, the present techniques are also applicable in other decision making contexts, both clinical and non-clinical in nature, where individual or collaborative decision making is practiced based on diverse information and where corporate or institutional memory of the decision and the decision making process are desirable.

In one implementation, a system in accordance with the present discussion may be developed and implemented using open source tools. Such a system may be developed as a web-based application, allowing distributed access or use of the application. For example, such an implementation may be developed using one or more of Java, Java server pages (JSP), structured query language (SQL), extensible markup language (XML), XML user interface language (XUL) and/or scalable vector graphics (SVG) technologies.

Figure 1:
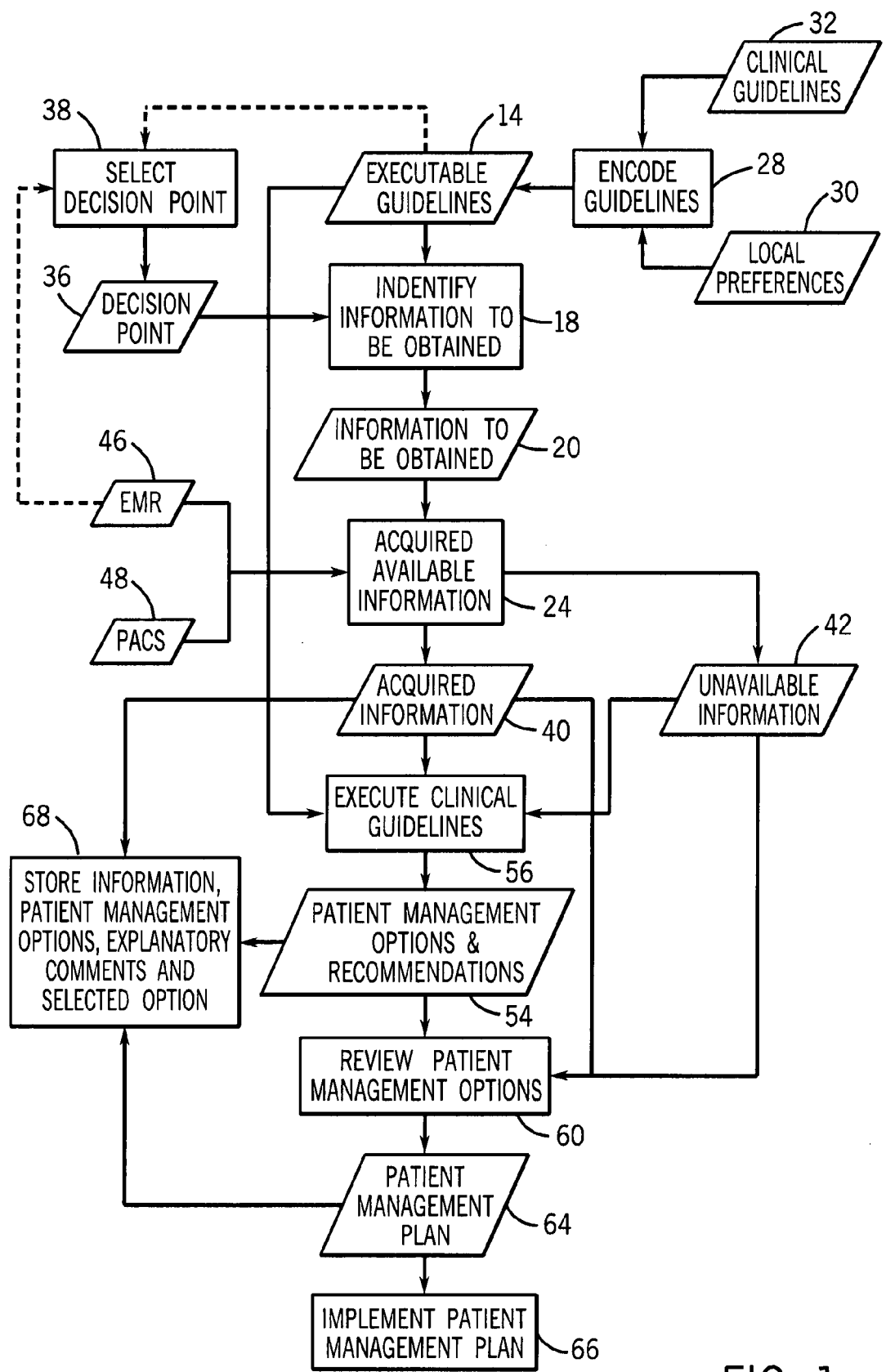
FIG. 1 is a flowchart depicted exemplary acts for deriving patient management options for a patient, in accordance with exemplary embodiments of the present technique.

The use of such a system in generating patient management options and in selecting a suitable patient management option is described with reference to FIG. 1. In particular, FIG. 1 depicts a flowchart 10 of exemplary actions taken in generating patient management options and in selecting a suitable patient management option in accordance with an embodiment of the present technique. In the depicted embodiment, a set of executable guidelines 14 are used to identify (block 18) relevant patient data 20 to be retrieved for analysis (block 24). In one embodiment, these executable guidelines 14 incorporate each of the decision points relevant to the management of a patient, along with the arguments used to make patient-specific recommendations at each decision point in view of the available data.

In an exemplary embodiment, the executable guidelines 14 are encoded in XML. In such an embodiment, the executable guidelines 14 may conform to an XML schema definition that facilitates exchanges between different locations, such as different hospitals or clinics. Further, in such an embodiment, though the executable guidelines 14 may be encoded in XML, executable routines that utilize the executable guidelines may be written in any suitable language or combination of languages. For example, an application configured to utilize the executable guidelines 14 may be written in Java and accessed via JSP.

In the depicted embodiment, the executed guidelines 14 are encoded (block 28) into an executable language (such as XML) from local preferences 30 (typically representing local practice at a facility or within a region) or clinical guidelines 32 (typically representing approved practice within a specialty or in the medical community at large). As will be appreciated, clinical guidelines 32 are typically based on the latest clinical evidence and relevant clinical trials and are intended to improve patient care by reducing unjustified, unsubstantiated, or improper variations in clinical practice. Typically clinical guidelines 32 are developed under the authority of a medical organization or government agency and are subsequently reviewed by a panel of experts. A combination of clinical guidelines 32 and local preferences 30 may be useful in forming the executable guidelines 14 in instances where one of the clinical guidelines 32 or local preferences 30 are insufficiently prescriptive or unambiguous and the other guideline or preference provides additional specificity and/or prescriptive power. In other instances, however, only one of local preferences 30 or clinical guidelines 32 may be encoded at block 28 to generate the executable guidelines 14. Further, as will be appreciated, local preferences 30 may vary from site to site and, as a result, executable guidelines 14 may also vary from site to site if some or all of the sites take into account their own local preferences 30.

In one embodiment, encoding the executable guidelines 14 at block 28 may involve integrating or converting the clinical guidelines 32 and/or local preferences 30 into an executable model configured for argument evaluation. For example, in such an embodiment, the executable guidelines 14 may be encoded as a set of executable for and against arguments for each potential patient management option. Such an argument evaluation implementation represents one possible approach to generating descriptive recommendations based on the executable guidelines 14.

For example, in one implementation, the executable guidelines 14 were encoded as a set of arguments based upon a combination of national clinical guidelines 32 (i.e. Association of Coloproctology of Great Britain and Ireland (ACPGBI, 2001), National Comprehensive Cancer Network (NCCN, 2006a, 2006b), National Cancer Institute (NCI, 2006a, 2006b)) and local clinical expertise 30. In this implementation, each of the clinical guidelines 32 was encoded into a set of self-sufficient arguments. Local clinical specialists from each of the relevant disciplines were interviewed to refine the combined set of clinical guidelines. The encoding of these guidelines into a set of logic statements, i.e., arguments, allowed them to be evaluated automatically, i.e., executed, for a given set of patient data.

As noted above, the executable guidelines 14 may be evaluated or processed to identify (block 18) the patient information that is needed to make the decision in question. Based on the executable guidelines 14, data with the potential to influence the clinical recommendations is identified at block 18. For example, in an embodiment in which the executable guidelines consist of various arguments associated with the different patient management options, the data needed to resolve the arguments may be identified at block 18 as information to be obtained 20. As an input to the identification process, a decision point 36 for a patient may be provided by a clinician. Alternatively, the decision point 36 may be a default decision point 36 automatically selected (block 38) based upon the executable guidelines 14. In other embodiments, the decision point 36 may be selected automatically (block 38) based upon a previous decision point or based upon data, diagnoses, or other information present in electronic medical records 46. Likewise, in some embodiments, the decision point 36 may be selected based upon previous entries in the decision support application. For example, if a patient has already been the subject of a previous meeting, the patient may be selected by a clinician from a list of available patients with some or all of the previous data recalled and presented visually to speed up entry and/or with the next sequential or likely decision point 38 selected.

As noted above a decision support application, including that portion of the application implementing the information identification process, may be implemented as a Java application accessed via JSP. In such an embodiment, based upon the decision point 36 provided, the executable guidelines 14 (such as a set of XML executable guidelines) are processed and provide as an output the information to be obtained 20, i.e., the relevant data for the decision to be made.

In the depicted embodiment, following the selection of the decision to be made for a patient and the resulting determination of the information needed to make the decision, the identified information 20 that is available is acquired (block 24). The acquired information 40 may be used in determining patient management options. As will be appreciated, however, not all of the information may be available. In other words some information 20 identified as having the potential to impact the patient management decision being made may not exist or may not be accessible. In one embodiment, such unavailable information 42 may be noted and/or tracked so that an indication of the information that is not available may be provided to the decision makers or so that an indication may be made when presenting patient management options that certain information that might impact the decision making process is not available.

In one embodiment, the identified information 20 is acquired by one or more electronic requests. In such an embodiment, a request may be a query to an electronic medical record (EMR) 46 or a picture archiving and communication system (PACS) 48, or may be a web-based form configured to electronically solicit the desired information from a relevant data store. As will be appreciated, an EMR 46 may include such information as patient history, patient demographic information, prescription records, test records and results, stored electronic monitoring data (such as pulse oximetry or electrocardiograph (ECG) data) and other stored electronic records of a medical nature related to the patient. Likewise, the PACS 48 may include raw or processed image data (including CAD processed images) from various modalities, such as computer tomography (CT), magnetic resonance imaging (MRI), positron emission tomography (PET), single-photon emission computed tomography (SPECT), X-ray, fluoroscopy, mammography, tomosynthesis, ultrasound, and/or PET/CT imaging systems.

In automated implementations, a decision support application may automatically gather the identified information 20 from an EMR 46 and/or a PACS 48 using published messaging protocols. In one example, such messaging protocols may include Health Level Seven (HL7) and/or digital imaging and communications in medicine (DICOM) standards to query electronic medical record databases for the identified information. In addition, in some implementations, algorithms or other extraction routines may be used to extract the relevant data from the data returned in response to the electronic queries. In such an embodiment, the algorithms or other extraction routines may be in the form of natural language processing for HL7 messages and image processing algorithms for DICOM images.

Conversely, in semi-automated implementations, the acquisition of the desired information may include notifying (such as via-e-mail or other electronic means) one or more clinicians to request that image studies from various imaging modalities, test data, laboratory results, or other relevant patient data be pre-loaded to the decision support application or to an accessible data storage location. Further, in such a semi-automated implementation, the pre-loaded data may be annotated ahead of time by a specialist to facilitate subsequent review by the MDT. In addition, data derived from specialist investigations may be summarized and provided to the decision support application by a clinician or other specialist. Such a summary may also describe the implications of the specialist investigation to the decision making process such that they may be presented clearly and accessibly to those members of the decision making team who are less knowledgeable about the specialty.

Once the acquired information 40 has been retrieved, it may be used to generate patient management options and recommendations 54, such as by execution (block 56) of the clinical guidelines 14 in view of the acquired information 40. In one embodiment, the executable guidelines 14 are implemented in a form suitable for argument evaluation such that each patient management option is associated with arguments for and/or against the patient management option. In such an embodiment, each argument may be provided in the form of a logic statement defining what combinations of values specific patient data may take to satisfy the argument. For example, an argument for the use of adjuvant chemotherapy in a patient with colorectal cancer might be that the patient is less than 80 years old.

In this exemplary argumentation model, such an argument might be one of many referring to a particular patient management option, in the instance discussed above, chemotherapy. For instance, in this example the patient may be less than 80 years old, arguing for chemotherapy. However, in another argument associated with the suitability of chemotherapy the patient might have a poor performance score, indicating an inability to endure the treatment and, thus, arguing against chemotherapy. In such an embodiment, therefore, it may be the preponderance or the relative distribution of satisfied arguments for and against each patient management option that identifies those options most recommended. Further, in some embodiments, certain arguments, or the different outcomes of such arguments, may be differentially weighted. For example, for a patient management option where five arguments determine whether the patient management option is recommended, some of the five arguments may be more influential than others in determining whether the patient management option is recommended, i.e., not all arguments are weighted equally in such an implementation. Likewise, a particular outcome for one argument, such as a drug allergy or genetic risk factor, may preclude recommendation of a patient management option, regardless of the outcome of other arguments related to the patient management option.

In embodiments employing argument-based executable guidelines 14, as described above, execution of the executable guideline 14 for a given patient and using the acquired information 40 may results in a series of "pros" and "cons" for each available patient management option. Such a list of patient management options associated with the relevant risks and benefits may be well suited to an individual or a group decision-making process, such as employed in MDT meetings, as the list provides a basis for discussion that is rooted in evidence-based medicine, i.e., the current clinical guidelines. As will be appreciated, the present techniques may also be employed in other decision making settings, whether group or individual in nature, where rules, guidelines, and/or preferences can be identified and encoded. For example, in a medical context, the present techniques may also be used in regular clinical practice, emergency room decision making, shift change transfer of information, and so forth. Likewise, though clinicians are discussed here as one possible audience for the decision support described herein, other staff or personnel (such as nurses, technicians, and other caregivers) may also utilize the present techniques in making patient management decisions.

In addition, information about the source of the arguments, and the associated list of "pros" and "cons", may be provided with each patient management option so that a reviewer can compare recommendations from each of the guidelines (or other source of an argument) as they make their decision. For example, in the context of the preceding chemotherapy argument, the recommendation for or against chemotherapy based on age may be presented with a visual or textual indication of the clinical guideline or guidelines that gave rise to the argument. In this manner, a reviewer may know at a glance whether an argument is based upon a national or international guideline, an older guideline, a local preference, and so forth, and may weight their assessment accordingly. This ability to distinguish between the origin of an argument (i.e. national guideline, local clinician preference) aids portability to different sites.

In addition, in listing or otherwise providing the patient management options and recommendations 54, each patient management option may be associated with visual or textual indications of the sufficiency of the evidence or data used in determining whether the patient management option is recommended. For example, if there is missing data or otherwise unavailable information 42 that, if present, might alter whether a patient management option is recommended or not, the patient management option may be presented visually or textually such that a reviewer can readily perceive that the recommendation, or lack of recommendation, is made based on incomplete evidence. For example, a recommendation regarding a patient management option may be made even though some data required by the arguments is missing. If the recommendation for the patient management option would change if the missing data had certain values, the recommendation may be visually displayed such that a reviewer can recognize the contingent basis of the recommendation. For instance, the recommendation associated with the patient management option may be color coded, such as presented in a colored font or with colored highlighting, to indicate the absence of complete data. Likewise, the recommendation associated with the patient management option may be differentiated with a marker or other visual indicator (such as an "*" or other marker beside the option or by use of underlined, italicized, and/or boldface text) to indicate the absence of complete data. Similarly, the recommendation associated with the patient management option may be accompanied by a textual comment indicating the nature of the missing data or indicating assumptions (such as data values) used in evaluating the relevant arguments in the absence of complete data. In such embodiments where the absence of complete information is brought to the notice of reviewers, the likelihood of errors of omission is reduced.

In addition to indicating the significance of missing data to the patient management options and recommendations 54, in some embodiments, the data or evidence having the greatest influence on a recommendation may also be emphasized, such as by color, textual emphasis, or other visual indications as described above. For example, in the context of colon cancer, data or evidence indicative of unresectable metastasis might preclude patient management options directed to an aggressive curative treatment of the primary tumour. Such precluded patient management options, therefore, might be color coded or textually or visually marked to allow a reviewer to easily identify patient management options in which evidence or data is essentially conclusive in character. Alternatively, to the extent that the data or evidence may be summarized or presented with the respective patient management options, highly influential data may be emphasized using color, textual emphasis, and/or visual markers to facilitate review. In such embodiments, emphasis on highly influential data or recommended patient management options can help direct the discussion of a panel of reviewers by focusing attention on the data with the greatest impact, and correspondingly directing attention away from data having little impact on the decision to be made, thereby improving the efficiency of the meeting.

Once the patient management options and recommendations 54 are generated (block 56) they are typically provided to a reviewer or a team of reviewers (such as clinicians) for review (block 60). For example, in one implementation a decision support application processes the executable guidelines 14 and the acquired information 40 to generate the patient management options and recommendations 54. In such an embodiment, the decision support application may include a meeting or presentation component that presents the patient management options and recommendations 54 to the clinician or team of clinicians.

In one embodiment, the meeting component provides an inherent workflow for the preparation and execution of a meeting of a team of decision makers, such as an MDT, as described here and below. For example, the meeting component may be configured to display some or all of the patient management options and recommendations 54, the acquired information 40, prior decisions (or decision history) and/or indications of what information is unavailable 42 in an integrated graphical user interface (GUI) for review by the team. In addition, the meeting components may include data update or entry capabilities, allowing the reviewers to update or add to the patient data in view of recent developments or in view of information generated during the meeting. In such an embodiment, the decision support application may be configured to automatically recalculate and present the treatment management options and recommendations in view of the new or updated patient data.

Further, the implementation of the meeting component may be distributed, allowing members of the MDT to participate from different locations. For example, in one embodiment the meeting component may be web-based or web-compatible, making the meeting component of the decision support application accessible over the Internet (or other network) for remote access and collaboration across geographically diverse locations. In one implementation, the meeting component may be developed using the XML user interface language (XUL). In addition, in some embodiments, the meeting component may include an image viewer that supports the plug-in of image analysis algorithms to assist image review. Likewise, in some embodiments image processing tools, such as segmentation and registration toolkits (like the Insight Segmentation and Registration Toolkit (ITK)), may be incorporated so that the results of the various image processing algorithms and tools can be automatically provided to the meeting participants.

In embodiments where the reviewers are provided with some or all of the acquired information 40 that was utilized in generating the patient management options and recommendations 54, this information may be presented in various ways. For example, acquired information 40 that is textual in nature may simply be provided as suitably formatted alphanumeric characters on a display or monitor or may be provided as a scanned image of the original documents. For acquired information 40 that is image-based, the decision support application may be configured to display the images, such as using the viewers and toolkits described above. In such embodiments, the decision support application may include or be integrated with medical image display and image analysis algorithms. Such algorithms may allow further analysis of the images within the meeting environment, such as image segmentation or CAD implementations, or may allow previous processing of the images to be properly displayed, such as CAD results or annotations by a radiologist.

The patient management options and recommendations 54 themselves may be provided to the reviewers in a ranked or unranked format or list. The recommendations for a patient management option may be provided as a qualitative value, such as "recommended" or "not recommended" or as a quantitative value, such as a score from 1 to 100. In one implementation, as discussed above, the recommendation for a patient management option may consist of a listing of the "pros" and "cons" (or "risks" and "benefits", "pluses" and "minuses", and so forth), associated with the patient management option, as discussed above. Indeed, such an implementation may be desirable to the extent that it facilitates discussion among the reviewers.

As noted above, listed patient management options or recommendations that might change if missing information was provided might be visually coded, such as by color, text, or some other visual indicator, so that reviewers are aware of the contingent nature of the recommendation. Likewise, some or all of the patient management options may include selectable links to the acquired information 40, clinical guideline 32, local preference 30, patient history, and so forth, that relates to the recommendation or commentary associated with that patient management option. In this way, a reviewer can quickly assess the context in which the patient management option was evaluated and the basis for the recommendation.

Based on a review (block 60) of the presented material, the reviewers may select a presented patient management option, may modify a presented patient management option, or may reject the presented patient management options, perhaps instead opting for a patient management option that was not presented by the decision support application. The accepted, modified, or new patient management option may form the basis for a patient management plan 64 which is followed in treating the patient (block 66). In one embodiment, the results of the review process, i.e., the selection, modification, or rejection of the patient management options and/or the introduction of a new patient management option, are recorded (block 68) for future reference. In such an embodiment, the acquired information 40 provided to the reviewers and the patient management options and recommendations 54 may also be stored (block 68) for future reference.

In instances where a presented patient management option is selected unanimously by the reviewers, the selected patient management may be incorporated into the patient management plan and a record of the selection stored (block 68) for future reference. In other situations, such as where a decision is not unanimous, where a patient management option which is not recommended is selected, or where all presented patient management options are rejected and a new patient management option is introduced by the reviewers, additional information or commentary may be stored (block 68). In this way, a comprehensive record of the decision-making process is maintained, which allows clinicians to quickly determine the result of previous decisions taken for a patient along with the clinician responsible for each decision and the evidence or reasoning on which the decision was based.

For example, in one embodiment, if a panel of reviewers, such as an MDT or other collaborative panel, selects a patient management option that is not supported by either the national guidelines 32 or local preferences 30 (as encoded in the executable guidelines 14), the panel may provide a reason for deviating from the guidelines or preferences. Likewise, in instances where there is no unanimous decision by the reviewers, an indication of which reviewers supported the decision and which reviewers dissented may be maintained. In addition, in such instances reviewers may provide comments or reasoning for their position, such as references to what available or unavailable information was determinative or influential to their position. This information may then be made available at subsequent decision meetings for that patient, thereby ensuring that all clinicians involved with making a patient management decision are fully aware of the previous decisions taken along with the information those decisions were contingent upon.

If the reviewers choose not to select a presented patient management option, the reviewers may reject the presented options and input the new patient management option they have selected. In such a circumstance, the application may request entry of which reviewers agreed upon the novel patient management option and/or which reviewers disagreed with selection of the novel patient management option. Likewise, the application may request that a reason be given for the selection of the non-presented patient management option, thus ensuring that accurate and useful records are kept when the reviewers, such as an MDT, deviate from the clinical guidelines 32 or local preferences 30. This information may then be made available for future review or reference, such as at a subsequent decision meeting.

In addition to being available for future decision meetings, the information that is stored (such as the presented patient management options, the acquired information, the selected option, dissenting opinions, commentary or reasons provided by reviewers, and so forth) may be useful in other contexts as well. For example, the stored information may constitute a comprehensive decision history, which may be construed as corporate or institutional memory, that includes a clear and complete record of each decision taken, the evidence on which this decision was made, an explanation of any deviation from the current clinical guidelines, and a record those clinicians supporting or dissenting from a decision. Such a comprehensive decision history represents a useful resource for auditing the decision process, revisiting previous decisions in light of new evidence, data-mining and/or reviewing efficacy or implementation of existing clinical guidelines 32 or local preferences.

Likewise, decision histories including such comprehensive information stored (block 68) by the application, may be useful in proposing new arguments or revising existing arguments to better-reflect best clinical practice. For example, the decisions taken for all or a subset of previous patients may be data mined for identifying relationships between patients and a graphical representation of the respective decisions made for each patient, allowing the most common pathways (i.e. series' of decisions) to be identified for a set of patients. Further the stored decision history may be used for tracking of patient decisions between shifts to facilitate shift transitions. Similarly, the stored decision history may be a useful mechanism for patient tracking decisions made in an emergency room context. In general, the stored decision history may be useful in any context where a history of the decisions made can aid in management of patients or transfer of knowledge.

For example, the decision history, particularly in a corporate or institutional setting, may be made available to other teams of decision makers, such as other MDTs, making decisions regarding a common patient. For example, the decision history generated by a colorectal MDT may be made available to an MDT addressing liver problems for the same patient. In this way, the decisions of both MDTs could be informed by the decisions and observations of the other MDT, even if the respective MDTs have no members in common.

With the foregoing in mind, an exemplary embodiment of a decision support application consistent with the above discussion was implemented using a relational database, MySQL, on which the guidelines and clinical data were stored. In this implementation, the relational database was accessed via the Java database connectivity (JDBC) application programming interface by the decision support application. The database was structured into two distinct sets of tables, those storing patient data and decision history and those storing the guidelines. In this implementation, the rule-base portion of the database may be made up of the decision, patient management option and argument tables to handle the decision support and the datatypes tables, which define the evidence over which the decision support logic can reason to generate patient management options, as described above.

In this implementation, each decision had a set of patient management options that were each in turn associated with a set of arguments. Each argument was provided as a logical rule defined in XML that referenced a subset of the datatypes. In this implementation, the datatypes table contained the set of patient data used to assess the patient management options. Each datatype could be constrained by a set of possible values of which either one or several might be selected. Based on these constraints, the graphical user interface for the application could generate a suitable input field for the datatype based on these constraints. Likewise, the ordering type, either cardinal, ordinal or discrete, was defined in this table for each datatype.

The other portion of the database included the tables for storing patient data values and decision history. For each decision point for every patient, all data available at the time of the meeting was stored along with patient management option selected, guideline support, and in the case of deviation from the guidelines, reasons for the deviation. Those clinicians in support of the decision were also recorded.

In accordance with this exemplary implementation, the workflow for a review meeting, such as an MDT meeting, may proceed generally as follows. The meeting component presents each patient that has been preloaded into the application for the meeting. The information presented for a patient is determined by the selected decision 36. Any imaging information that has been preloaded, such as from PACS 48, is also provided. In addition to the patient information, the decision history for the patient is displayed if previous decisions have been made for the patient using the decision support application. When present, the decision history details each decision previously made for the patient along with the evidence relevant to making that decision. Following a review of the patient information, the application displays all available options for the decision (based upon the preloaded guidelines 14) along with the generated recommendations. In one implementation, to aid decision making, a set of descriptive arguments is generated for each option that either supports or opposes the option. If prior decisions have been made for the patient, the arguments are presented (which may include a relevancy score which indicates the previous support for the argument by the clinicians). In addition to the set of options, the application also warns the reviewers of any information that was not preloaded for the patient, i.e., information that was unavailable, and how this information might affect the recommendations. The reviewers may then select a recommended option, a non-recommended options (with the proviso that a reason is given for opposing the recommendations), or create and select a new option. The final decision is then recorded by the application along with the relevant arguments and any additional comments entered by the reviewers.

Exemplary screen views are provided in FIGS. 2-6 to illustrate how such an implementation might be presented to a panel of decision makers, such as an MDT, for review using a graphical user interface. In the depicted implementation, the provided screen views are suitable for presentation on a display or monitor, such as may be found on a computer or medical workstation, or for presentation via a projector onto a wall or large screen. For example, referring to FIG. 2, a presentation might be provided in a tabbed format, allowing the reviewers to flip between tabs as desired to see different information that is available for the patient. As depicted in the exemplary screen views, a presentation may begin with a patient summary screen 100 that is selectable via a summary tab 102 at the top of the screen. Information provided on the patient summary screen 100 may include a short narrative introduction 104 to the patient along with preliminary information 106 regarding their clinical presentation (e.g. name, age, gender, symptoms etc.). In addition, certain patient information 108 may be provided throughout the presentation, such as at the top of each page, to facilitate the review and discussion process. For example, the recurrent patient information 108 may include name, age, sex, current estimate of tumor stage, and so forth.

Figure 3:
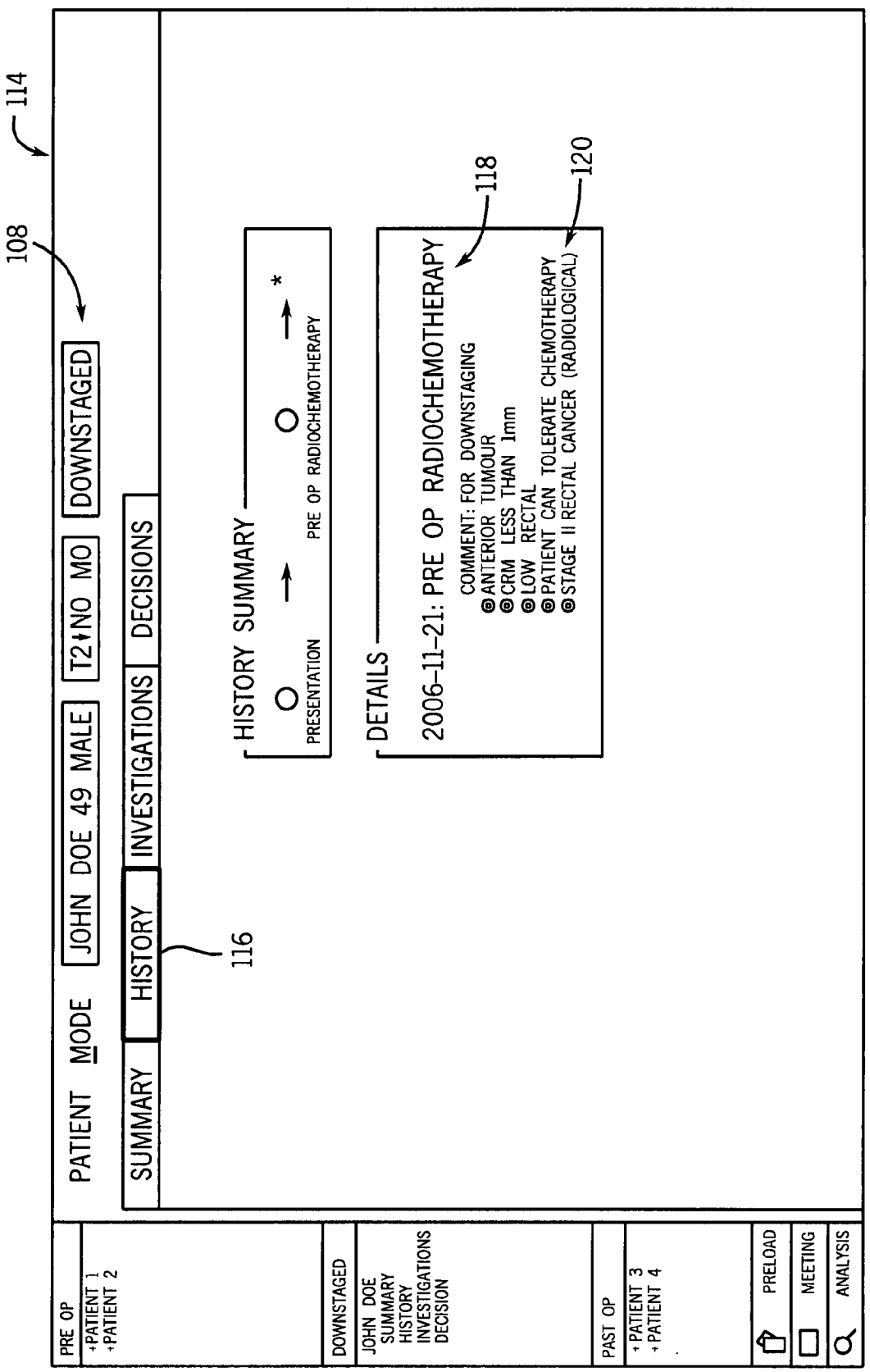
FIG. 3 is an exemplary screenshot of a decision history for review in selecting a patient management option, in accordance with exemplary embodiments of the present technique.

In an exemplary presentation, the reviewers might next review the decision history for the patient, as depicted on exemplary decision history screen 114 shown in FIG. 3, that is selectable via a history tab 116 at the top of the screen. Information provided on the decision history screen 114 may include a review of any previous decisions 118 taken by the MDT for that patient along with any commentary 120 or reasoning provided for that previous decision. In the depicted example, the decision history describes a previous decision 118 that the patient undergo pre-operative radiochemotherapy. The basis for that decision, evidenced in commentary 120, included such factors as tumour location, margin, stage and patient fitness.

Figure 4:
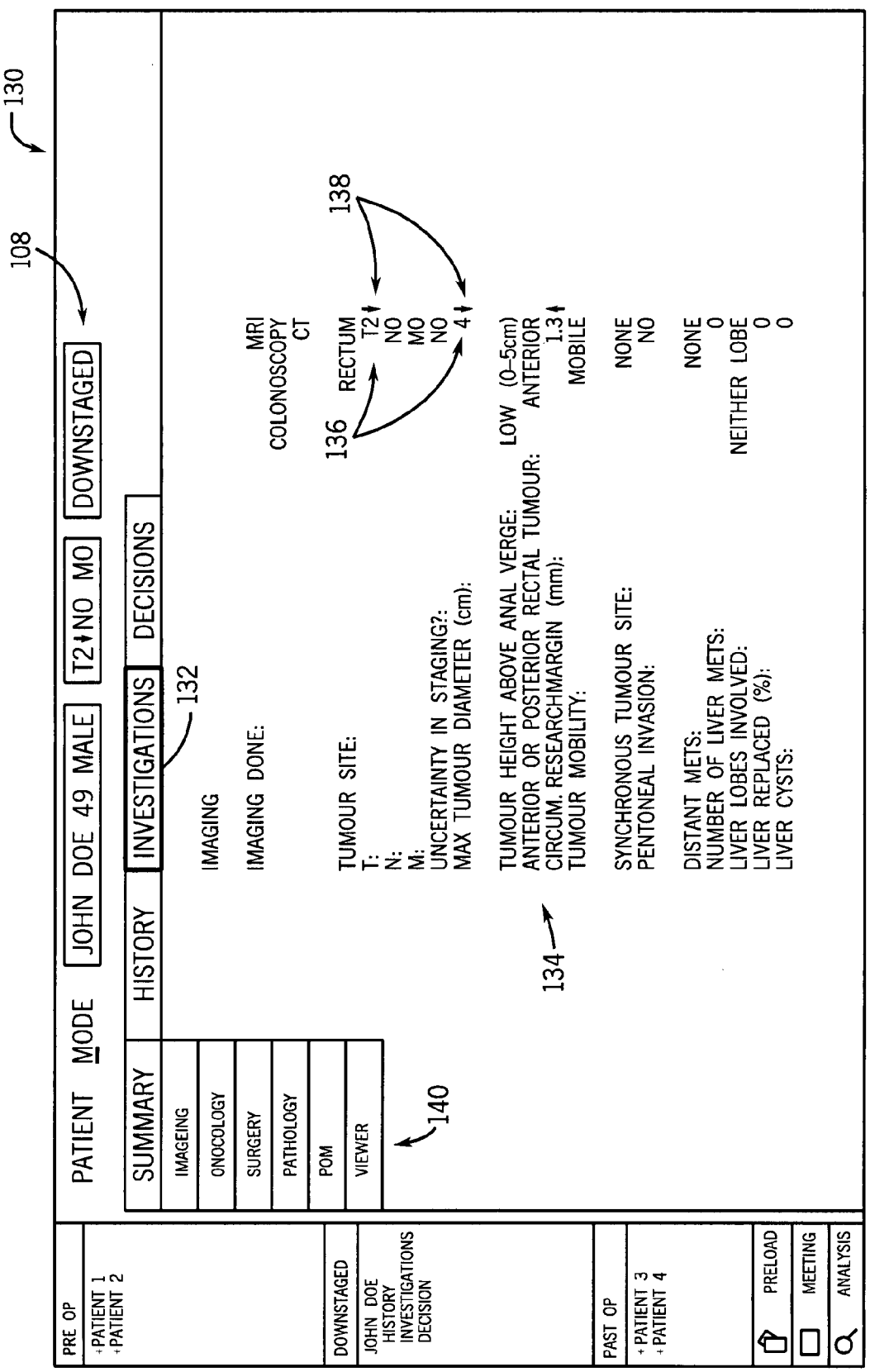
FIG. 4 is an exemplary screenshot of patient data for review in selecting a patient management option, in accordance with exemplary embodiments of the present technique.

The reviewers in the exemplary presentation might next review the evidence available for the present decision, as depicted on the exemplary investigations screen 130 shown in FIG. 4, that is selectable via an investigations tab 132 at the top of the screen. Information provided on the investigations screen 130 may include all data relevant to the present decision. In the depicted example, the relevant data is subdivided by specialty, with the data 134 derived from imaging studies (i.e. CT, MRI and colonoscopy) presented in the depicted exemplary investigations screen 130. In this example, the relevant data associated with each specialty is selectable by tabs or buttons 140 along the side of the screen. In this manner, the reviewers may flip between the different relevant data, as broken down by specialty, at their convenience.

In addition, in the depicted example, the application has visually indicated changes in the imaging data from previous imaging studies, which might be of particular interest to a reviewer. For example, the application has visually emphasized (here with bold text 136 and associated arrows 138 indicating the direction of the change) that the both the tumour's T stage and size have decreased, while the resection margin has increased. As will be appreciated, other visual mechanisms may be employed to draw attention to data of particular interest, such as where there have been changes in the data or where new data is available. For example, color-coded text or background highlighting or different font emphasis, such as italics, underlining, boldface and so forth, may be employed.

Figure 5:
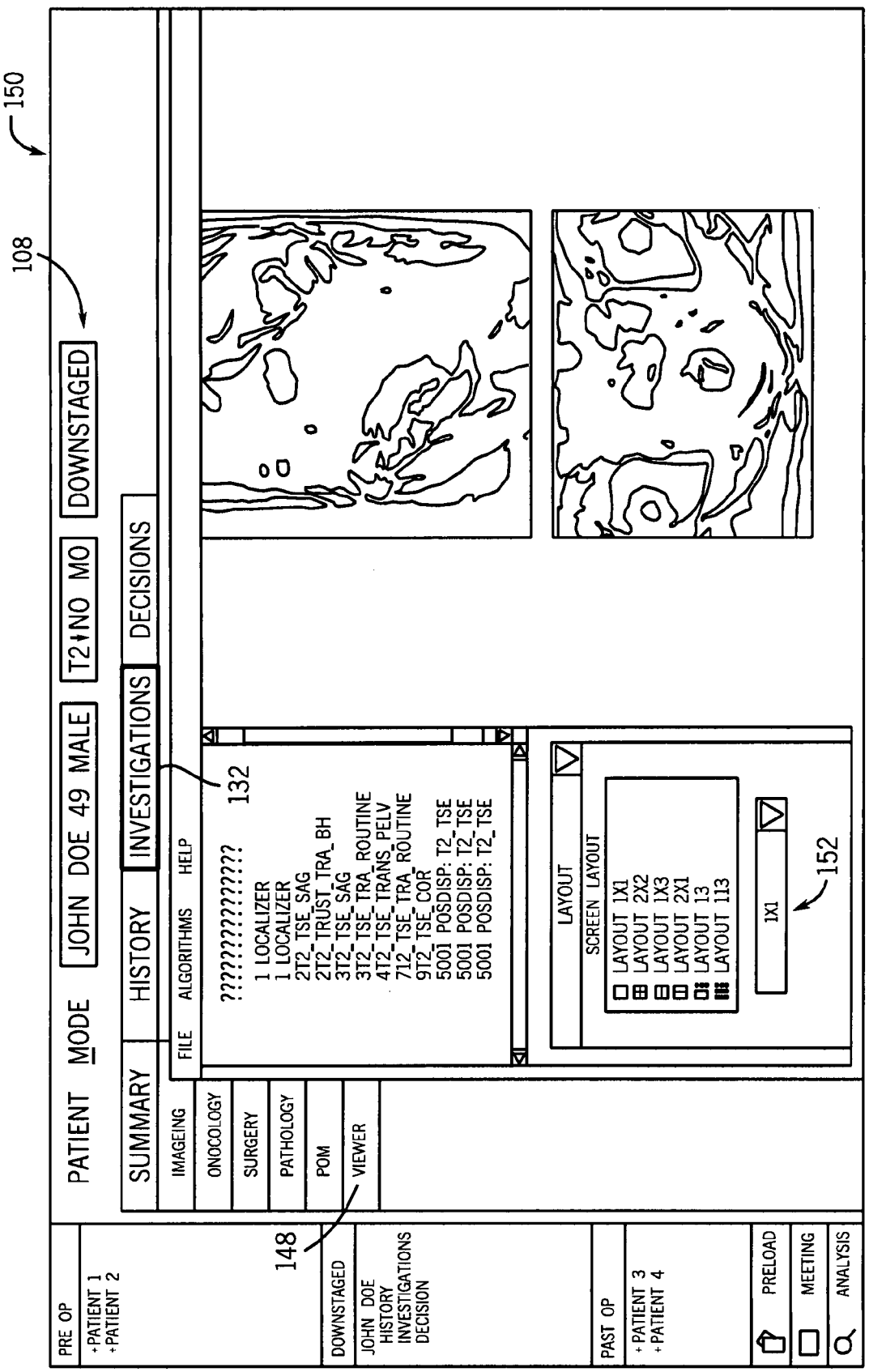
FIG. 5 is an exemplary screenshot of imaging data for review in selecting a patient management option, in accordance with exemplary embodiments of the present technique.

In the depicted exemplary investigations screen 130, a viewer option 148 is also provided, as shown in FIG. 5. In the present example, selection of the viewer option 148 by a reviewer presents the reviewer with an integrated DICOM viewer that allows DICOM compatible images 150 that have been loaded into the application to be displayed on the screen. As will be appreciated other viewers that enable or facilitate the display of images of interest may be provided in addition to or instead of the DICOM viewer. Further, image viewing tools 152 may also be provided to the reviewers to allow manipulation of the presentation or analysis of the images 150.

Figure 6:
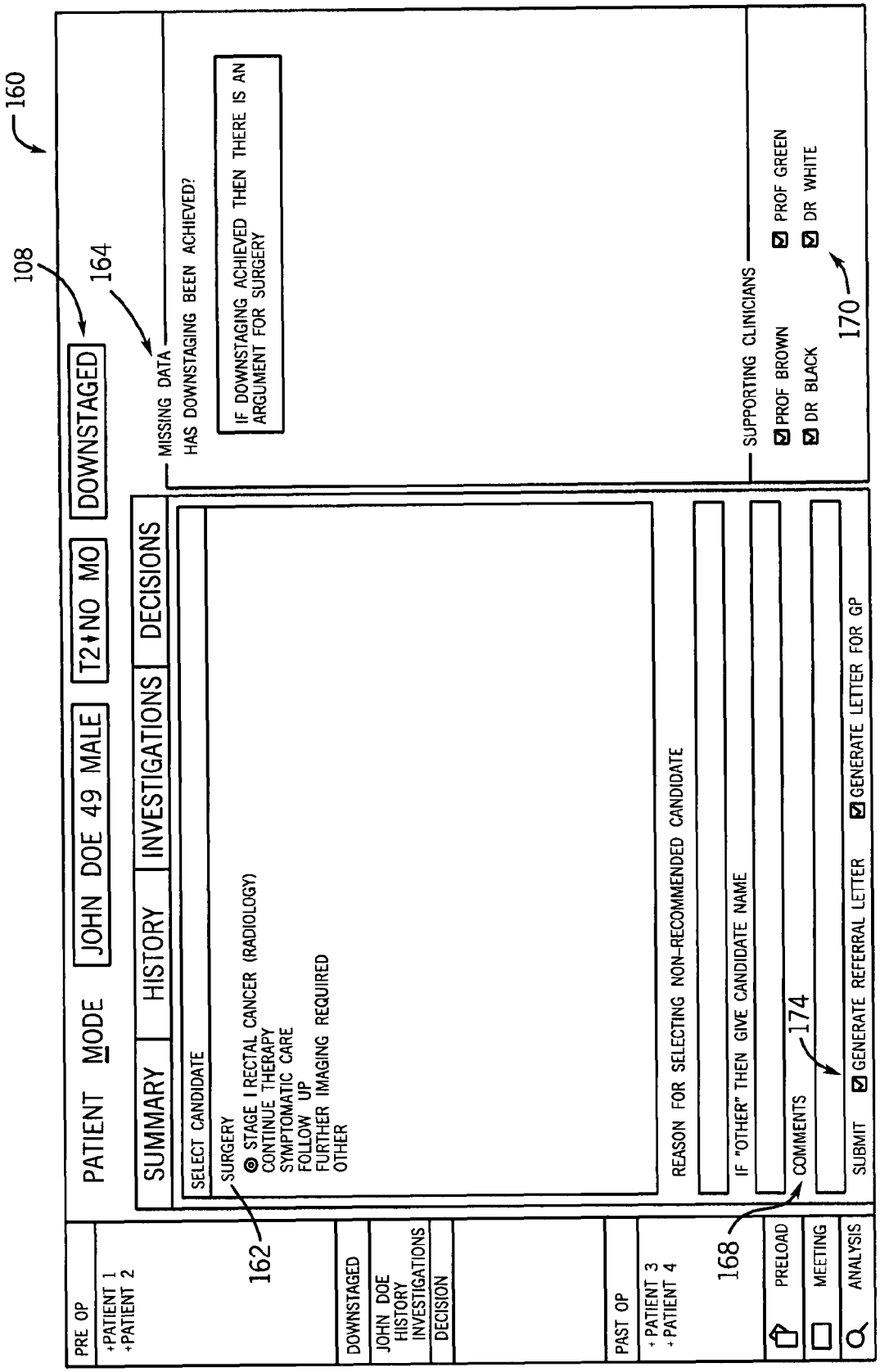
FIG. 6 is an exemplary screenshot of a patient management option selection screen, in accordance with exemplary embodiments of the present technique.

The reviewers in the exemplary presentation might next select a patient management option, as depicted on the exemplary decision screen 160 shown in FIG. 6, that is selectable via a decision tab 132 at the top of the screen. In the depicted example, the decision screen 160 presents the recommendations 162 generated by the application based on the latest clinical guidelines. In this example, surgery is the only recommended candidate (denoted by the visual check 162 beside the option) based on the stage of the tumour, with any potential arguments against this option no longer relevant to the patient, following downstaging. The decision screen 160 may also present an indication of what data or information is missing 164 (in this example, whether downstaging has been achieved) and indicates how this information could affect the recommendations.

The exemplary decision screen 160 also provides for the entry of comments at comment block 168, either in support of the selected patient management option or a patient management option that was not selected or against the selected patient management option. Likewise, the exemplary decision screen 160 allows individual members of the reviewing panel, such as an MDT, to indicate their support for a decision, such as with the depicted check boxes 170. Conversely, those reviewers who do not support a decision may refrain from indicating their support.

Once the decision has been made, the application may allow certain administrative functions to be automatically performed based on the decision. For example, in the depicted example, the decision screen 160 allows for the automatic generation of certain letters (for example, patient management referral letters, letters to inform the primary care physician of the MDT's decision, or personalized patient information letters) upon selection of a patient management option. In one embodiment, such letters or other administrative functions may be selected via a user selectable mechanism, such as check boxes 174. As will be appreciated, other administrative or medical follow up actions may also be automated in this manner upon selection of a patient management option.

As will be appreciated by those of ordinary skill in the art, the preceding discussion and accompanying screen views merely depict an exemplary presentation. While such features as selectable tabs, check boxes, and certain types of visual indicators or emphasis have been depicted for the sake of explanation, other types of selection mechanisms or emphasis techniques are also contemplated and are clearly within the scope of the present technique. Indeed, any mechanism common to application development that is suitable for use in indicating a selection, for moving between aspects of a data presentation, or for providing visual or auditory emphasis are suitable for use with the present technique.

Figure 7:
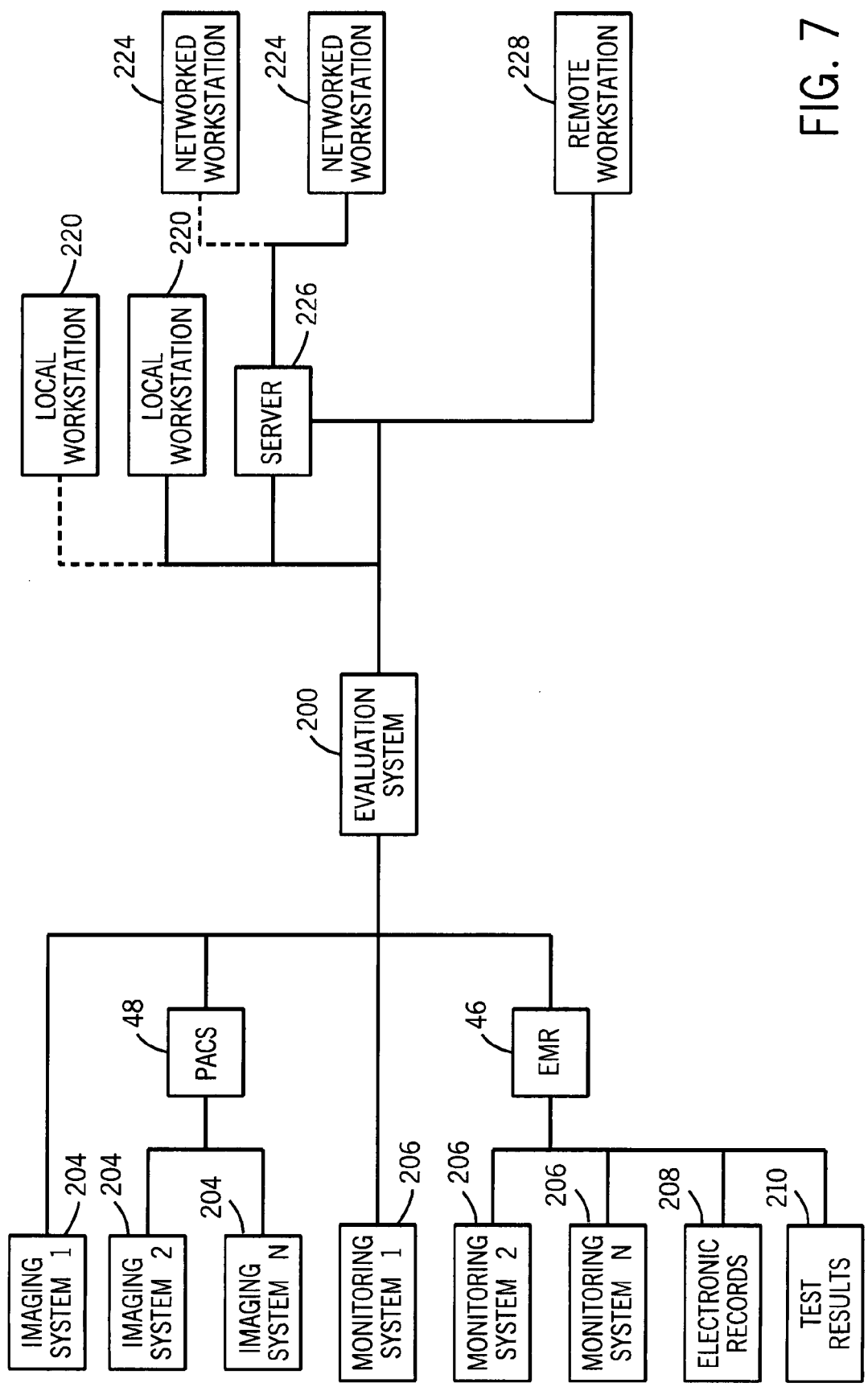
FIG. 7 is a block diagram depicting an exemplary communication infrastructure, in accordance with exemplary embodiments of the present technique.

With the foregoing in mind, it will be appreciated that the decision support application may be provided as part of an evaluation system 200, as depicted in FIG. 7. As will be appreciated, the evaluation system 200 may be a processor-based system, such as a general purpose computer executing routines for implementing the functions of the decision support application as described above. Conversely, the decision support application may be an application specific computer or workstation configured specifically for performing the functions of the decision support application as described above, such as by executing routines implementing these functions, and/or by incorporating certain application specific circuitry, i.e., firmware or hardware, that encode such functionality. In general embodiments, however, the evaluation system 200 is provided as a processor-based system having one or multiple processors that execute routines implementing the decision support application. Such routines may be stored in the evaluation system 200 on one or more suitable storage devices (such as on one or more hard drives, one or more optical drives, dedicated memory, and so forth). Alternatively, some or all of the routines for implementing the decision support application may be stored remote from the evaluation system, such as on a server, or other network accessible data repository. As will be appreciated by those of ordinary skill in the art, in practice, the various routines for implementing the decision support application described herein may be stored on one or multiple machine-readable media which may be entirely, partially or not at all local to the evaluation system 200.

Such an evaluation system 200 may be configured to communicate with a variety of devices to perform the functions described herein. For example, as noted above, the evaluation system 200 may be configured to communicate with a PACS 48. The PACS 48 may in turn be configured to communicate with one or more imaging systems 204, such as MRI, PET, CT, SPECT, PET/CT, tomosynthesis, mammography, and/or ultrasound systems, for example. Likewise, in some embodiments, such as embodiments where no PACS 48 may be present, the evaluation system 200 may be configured to communicate directly with one or more of the imaging systems 204.

Likewise, the evaluation system 200 may be configured to communicate with an EMR 46, as noted above. The EMR 46 may in turn be configured to communicate with one or more monitoring systems 206, to one or more sources of electronic medical records 208 (such as hospital records of patient history), and/or to one or more electronic sources of test or lab results 210. As will be appreciated, in the absence of a singular or consolidated EMR 46, one or more of such underlying sources of patient information may be configured to communicate directly with the evaluation system 200.

While the preceding describes the types of systems the evaluation system 200 might be configured to communicate with to request patient information in support of a decision support application executed on the evaluation system 200, the evaluation system 200 also communicates with downstream devices for presenting the results of its analysis and for receiving feedback from the reviewers. As noted above, the presentation routines executed by the evaluation system 200 may be provided to a decision meeting at one location or to collaborative decision makers who are separated from one another. To this end, the evaluation system 200 may be configured to communicate with various downstream workstations or servers. For example, the evaluation system 200 may be configured to communicate directly with a local workstation 220 over dedicated lines or via wireless communication (depicted via dotted line). Likewise, the evaluation system 200 may communicate with one or more networked workstations 224 used by the collaborative decision makers via an intermediary server 226. Such an embodiment may be employed in a networked hospital environment. Similarly, the evaluation system 200 may communicate with one or more remote workstations 228, i.e., geographically remote workstations, via a direct internet connection or via a server 226 connected to the internet. In this manner, the evaluation system 200 may communicate with one or more workstations employed by the collaborative decision makers involved in making a decision. Furthermore, such diverse downstream access may enable the opportunistic involvement of an expert at a remote site, not ordinarily part of the MDT or other collaborative panel, to contribute to the management of individual patients.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for generating patient management options, the method implemented on a physical computer, said method comprising:
    encoding, using a processor, a set of clinical guidelines and a set of local preferences to generate a set of encoded guidelines;
    identifying information to be obtained, wherein the information is identified based at least on the set of encoded guidelines;
    electronically acquiring, using a processor, the information that is available and noting information that is unavailable;
    generating, using a processor, one or more patient management recommendations by executing the set of encoded guidelines and analyzing the acquired information and the unavailable information;
    providing the one or more patient management recommendations to one or more decision makers, said patient management recommendations comprising options and argument evaluations for or against the patient management options; and
    providing an indication of the unavailable information and an indication of a potential impact on the one or more patient recommendations of the unavailable information.

2. The method as recited in claim 1, wherein electronically acquiring the information that is available comprises electronically acquiring the information from at least one of an imaging system, a monitoring system, a picture archiving and communication system, or an electronic medical records system.

3. The method as recited in claim 1, further comprising storing at least the one or more patient management recommendations, the available information, the indication of the unavailable information, and a selected patient management option.

4. The method as recited in claim 1, further comprising storing at least the one or more patient management recommendations, the available information, the indication of the unavailable information, contingent information related to the one or more patient management recommendations, a selected patient management option, and one or more comments related to the selection or rejection of a respective patient management recommendation.

5. The method of claim 4, wherein the stored information is a decision history that may be used for patient management or transfer of patient knowledge.

6. The method as recited in claim 1, wherein the one or more decision makers comprises a multidisciplinary panel of reviewers or other care-giving team.

7. The method as recited in claim 1, further comprising providing an indication of a potential impact on the one or more patient recommendations of at least one of a decision history and the acquired available information.

8. The method as recited in claim 1, further comprising treating a patient using a selected or modified patient management option from the one or more patient management recommendations.

9. A computer program encoded on one or more non-transitory computer readable media, the computer program executed on a computer and implementing a method comprising:
   forming a set of encoded guidelines to identify information to be obtained, wherein the set of encoded guidelines comprises at least one encoded set of clinical guidelines and an encoded set of local preferences;
   acquiring the information that is available and noting information that is unavailable;
   generating one or more patient management recommendations based upon the set of encoded guidelines, the available information, and the unavailable information;
   providing the one or more patient management recommendations to one or more decision makers, said patient management recommendations comprising options and argument evaluations for or against the patient management recommendations; and
   providing an indication of the unavailable information and an indication of a potential impact on the one or more patient recommendations of the unavailable information.

10. The computer program as recited in claim 9, wherein acquiring information accesses at least one of an imaging system, a monitoring system, a picture archiving and communication system, or an electronic medical records system using published messaging protocols.

11. The computer program as recited in claim 9, wherein generating the one or more patient management recommendations executes the encoded guidelines.

12. The computer program as recited in claim 9, further comprising storing at least the one or more patient management recommendations, the acquired available information, the indication of the unavailable information, and a selected patient management option.

13. The computer program as recited in claim 9, further comprising storing at least the one or more patient management recommendations, the acquired available information, an indication of the unavailable information, a selected patient management option, and one or more comments related to the selection or rejection of a respective patient management option.

14. A processor-based system, comprising:
   one or more memory or storage components configured to store routines, wherein the routines execute a set of encoded guidelines identifying information to be obtained, said set of encoded guidelines comprising at least one encoded set of clinical guidelines and an encoded set of local preferences, electronically acquiring information that is available and noting information that is unavailable, executing the set of encoded guidelines and generating one or more patient management recommendations based upon the set of encoded guidelines, the available information and the unavailable information, and providing the one or more patient management recommendations along with an indication of the unavailable information and an indication of a potential impact on the one or more patient recommendations of the unavailable information to a multidisciplinary panel of reviewers;
   one or more communication interfaces allowing communication between the processor-based system and other devices connected directly to the processor-based system or connected via one or more networks; and
   one or more processors executing the routines stored on the one or more memory components and communicating with the other devices for acquiring the information and/or and for providing the one or more patient management recommendations for display.

15. The processor-based system as recited in claim 14, wherein the other devices comprise at least one of an imaging system, a monitoring system, a picture archiving and communication system, an electronic medical records system, a server, or a workstation.

16. The processor-based system as recited in claim 14, wherein the one or more memory or storage components further comprise storing at least the one or more patient management recommendations, the available information, the indication of the unavailable information, and a selected patient management option.

17. The processor-based system as recited in claim 14, wherein the one or more memory or storage components further comprise storing one or more comments related to the selection or rejection of respective patient management recommendations by the multidisciplinary panel of reviewers.

* * * * *